US007968053B2

United States Patent
Hayashi et al.

(10) Patent No.: US 7,968,053 B2
(45) Date of Patent: Jun. 28, 2011

(54) CHLORINE ANALYZING APPARATUS

(75) Inventors: Norio Hayashi, Chigasaki (JP);
Takayuki Okafuji, Chigasaki (JP);
Tamaki Tomoyose, Chigasaki (JP);
Shuichi Akasaka, Chigasaki (JP)

(73) Assignee: Mitsubishi Chemical Analytech Co., Ltd., Yokkaichi-shi, Mie-ken (JP)

( * ) Notice: Subject to any disclaimer, the term of this patent is extended or adjusted under 35 U.S.C. 154(b) by 1153 days.

(21) Appl. No.: 11/712,551

(22) Filed: Mar. 1, 2007

(65) Prior Publication Data
US 2007/0224086 A1    Sep. 27, 2007

(30) Foreign Application Priority Data

Mar. 22, 2006  (JP) .................................. 2006-078066
Nov. 16, 2006  (JP) .................................. 2006-310156

(51) Int. Cl.
*G01N 27/44* (2006.01)
(52) U.S. Cl. ......................... 422/75; 205/788.5
(58) Field of Classification Search ............... 422/75; 205/788.5
See application file for complete search history.

(56) References Cited

U.S. PATENT DOCUMENTS

| 2,856,426 A | * | 10/1958 | Estabrook .................... 562/896 |
| 4,772,758 A | * | 9/1988 | Kaufhold ..................... 585/803 |
| 2004/0126729 A1 | | 7/2004 | Hayashi | |

FOREIGN PATENT DOCUMENTS

| EP | 1 403 636 A2 | 3/2004 |
| JP | 58-162854 A | 9/1983 |
| JP | 2003-126228 A | 5/2003 |

OTHER PUBLICATIONS

Wegman et al, "The microcoulometric determination of extractable organic halogen in surface water; application to surface waters of the Netherlands", The Science of Total Environment, vol. 71, No. 3, May 1, 1977-Jan. 31, 1977, pp. 235-245, XP007913265.
Extended European Search Report in EP 07 00 4808 dated Jun. 14, 2010.

* cited by examiner

Primary Examiner — In Suk Bullock
Assistant Examiner — Paul S Hyun
(74) Attorney, Agent, or Firm — Nixon & Vanderhye P.C.

(57) ABSTRACT

A chlorine analyzing apparatus includes a reaction tube of a double tube structure with an inner tube for receiving a sample and an outer tube for recovering hydrogen chloride. An electric furnace has a reaction tube insertion hole into which the reaction tube is inserted. The electric furnace is equipped with a heater disposed around the reaction tube insertion hole. A titration cell receives acetic acid as an electrolyte and subjects hydrogen chloride withdrawn from the reaction tube to coulometric titration. A deodorization tube is disposed on a rear stage side of the titration cell for thermally decomposing a vapor of acetic acid discharged from the titration cell. The deodorization tube is fitted into the electric furnace.

14 Claims, 3 Drawing Sheets

A-A SECTION

CHLORINE ANALYZING APPARATUS

BACKGROUND OF THE INVENTION

The present invention relates to a chlorine analyzing apparatus, and more particularly, to a chlorine analyzing apparatus for measuring a trace amount of chlorine using a coulometric titration method.

A trace amount of chorine compounds contained in environmental water such as river water and lake water or waste water discharged from various factories has been measured, for example, by flowing a liquid sample through a column filled with activated carbon to adsorb a chlorine compound contained in the liquid sample into the activated carbon using a chlorine absorber and then subjecting the chlorine compound adsorbed into the activated carbon to coulometric titration using a chlorine analyzer. More specifically, the activated carbon as a sample is filled in a reaction tube, and the reaction tube is fitted into an electric furnace to heat the sample under an oxygen flow, thereby burning the chlorine compound contained in the sample and converting the chlorine compound into hydrogen chloride. Thereafter, the thus generated hydrogen chloride is adsorbed in an electrolyte filled in a titration cell and titrated with silver ions coulometrically generated in the titration cell. The amount of chlorine can be calculated from a quantity of electricity required for the titration on the basis of Faraday Rule (refer to "Method for Measuring Chlorine (Vertical-type Furnace Coulometry Method)", Dia Instruments Co., Ltd.; [online]; searched on Mar. 3, 2006; Internet <http://www.dins.co.jp/dins_j/3sehin/genri/gts300cl.htm>). Meanwhile, acetic acid is used as the electrolyte to be filled in the titration cell.

In the above chlorine analyzing apparatus, with the introduction of hydrogen chloride into the titration cell, a vapor of acetic acid is discharged from the titration cell. However, it may be difficult to completely treat the vapor of acetic acid until becoming odorless even though the vapor of acetic acid is subjected to neutralization treatment using a removing device. If a treating performance of the removing device is increased, there tends to arise such a problem that the size of the removing device must be enlarged.

SUMMARY OF THE INVENTION

The present invention has been made in view of the above conventional problems. An object of the present invention is to provide a chlorine analyzing apparatus for measuring a trace amount of chlorine contained in a sample by subjecting hydrogen chloride generated by heating the sample to coulometric titration in acetic acid as an electrolyte which is capable of surely and efficiently treating a vapor of acetic acid discharged from the titration cell.

To solve the above problems, in the present invention, a vapor of acetic acid discharged from a titration cell is decomposed by heat generated from an electric furnace for heating a reaction tube, whereby the vapor of acetic acid can be efficiently treated without increase in a size of the apparatus used therefor.

Thus, in accordance with the present invention, there is provided a chlorine analyzing apparatus for measuring an amount of chlorine contained in a sample by subjecting hydrogen chloride generated by heating the sample to coulometric titration, which apparatus comprises mainly a reaction tube of a double tube structure comprising an inner tube with an inlet port for air or oxygen for receiving the sample, and an outer tube with a sampling gas outlet port for recovering hydrogen chloride, the reaction tube being capable of allowing a gas to be flowed from the inner tube to the outer tube;

an electric furnace having a reaction tube insertion hole into which the reaction tube is fitted, which is equipped with a heater disposed around the reaction tube insertion hole; and a titration cell receiving acetic acid as an electrolyte for subjecting hydrogen chloride withdrawn from the reaction tube to coulometric titration, said apparatus further comprising a deodorization tube disposed on a rear stage side of the titration cell for thermally decomposing a vapor of acetic acid discharged from the titration cell, which is fitted into the electric furnace.

EXPLANATION OF REFERENCE NUMERALS

1: Reaction tube; 11: Inner tube; 12: Sample feed portion (sample feed port); 13: Inlet port for air or oxygen; 14: Outer tube; 15: Sampling gas inlet port; 3: Titration cell; 31: Cooler; 4: Deodorization tube; 6: Dryer; 7: Removing device; 8: Vacuum pump; 9: Electric furnace; 91: Reaction tube insertion hole; 92: Heat-insulating material; 93: Heater; 94: Deodorization tube insertion hole; P: Sample

DETAILED DESCRIPTION OF THE INVENTION

Figure 1:
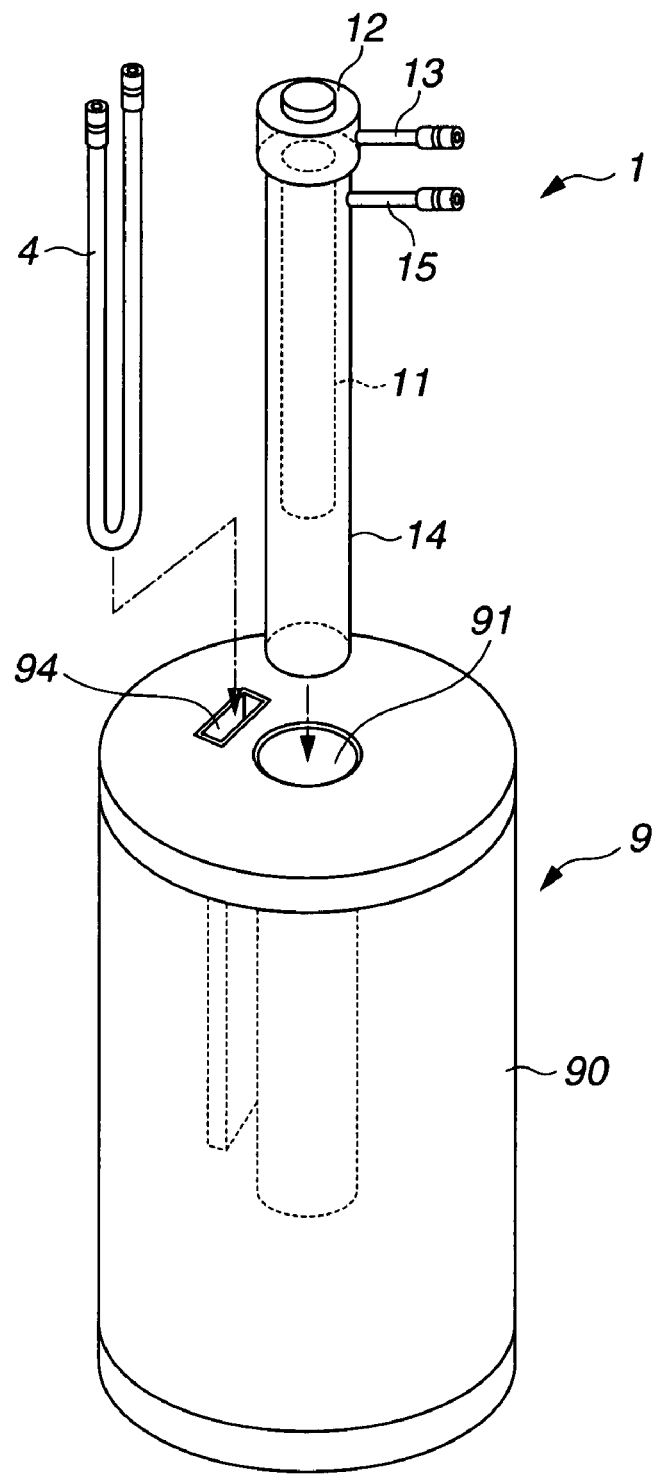
FIG. 1 is a perspective view showing an electric furnace, a reaction tube and a deodorization tube provided in a chlorine analyzing apparatus of the present invention.
Figure 2:
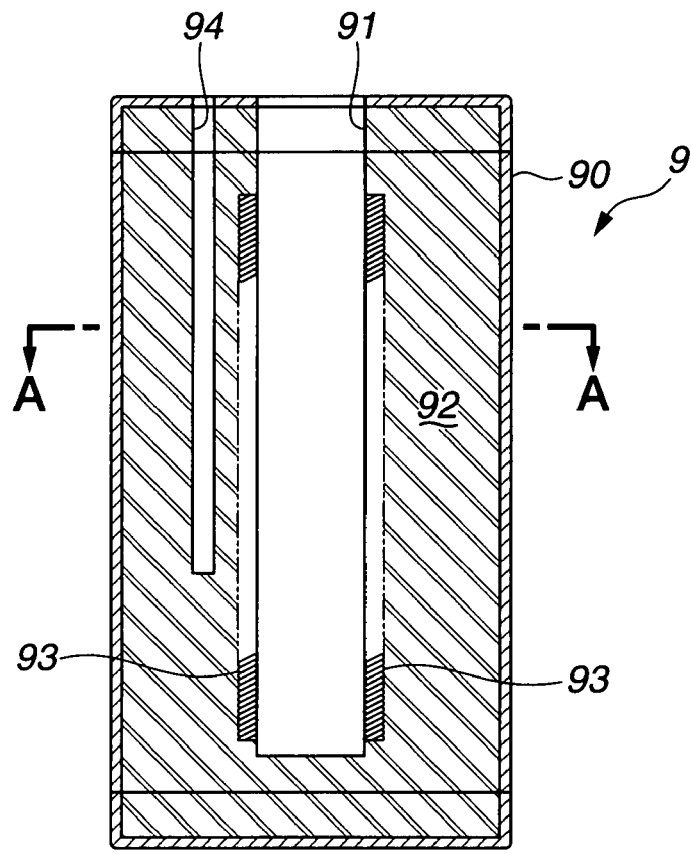
FIG. 2 is a vertical sectional view and a horizontal sectional view showing a structure of an electric surface provided in a chlorine analyzing apparatus of the present invention.
Figure 2:
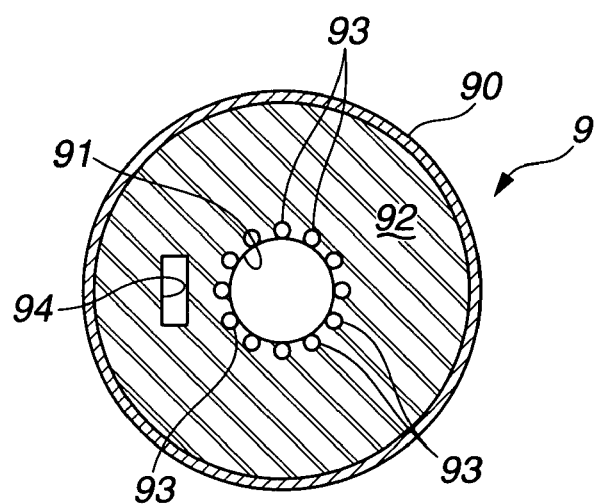
Figure 3:
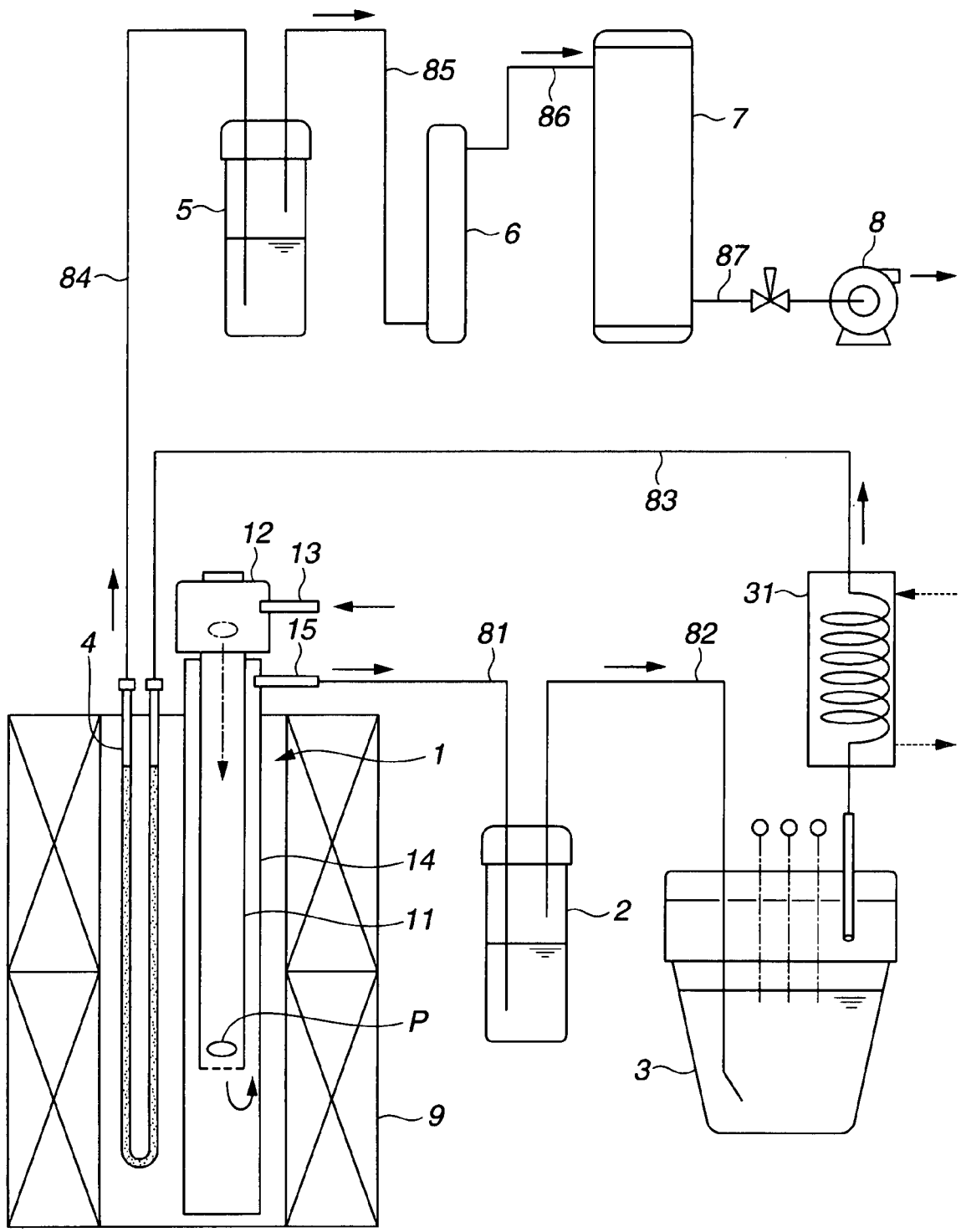
FIG. 3 is a flow diagram schematically showing a whole structure of a chlorine analyzing apparatus of the present invention.

A preferred embodiment of the chlorine analyzing apparatus of the present invention is described below by referring to the accompanying drawings. FIG. 1 is a perspective view showing an electric furnace, a reaction tube and a deodorization tube provided in the chlorine analyzing apparatus of the present invention. FIG. 2 is a vertical sectional view and a horizontal sectional view showing a structure of the electric surface provided in the chlorine analyzing apparatus of the present invention. FIG. 3 is a flow diagram schematically showing a whole structure of the chlorine analyzing apparatus of the present invention.

The chlorine analyzing apparatus of the present invention is an analyzer for measuring an amount of chlorine contained in a sample by subjecting hydrogen chloride generated by heating the sample to coulometric titration. As shown in FIG. 3, the chlorine analyzing apparatus generally includes a reaction tube (1) for receiving a sample (P), an electric furnace (9) for heating the reaction tube, and a titration cell (3) for conducting titration of the sample, and in the apparatus, a vapor of acetic acid discharged from the titration cell (3) is decomposed in a deodorization tube (4). Meanwhile, in the present invention, activated carbon into which a chlorine compound is adsorbed is usually used as the sample (P).

The reaction tube (1) is a container which serves for not only receiving the above sample (P), but also burning a chlorine compound contained in the sample to recover hydrogen chloride. As shown in FIGS. 1 and 3, the reaction tube (1) has a double tube structure constituted of an inner tube (11) for receiving the sample and an outer tube (14) for recovering hydrogen chloride therefrom.

The inner tube (11) is constituted of an elongated cylindrical tube provided at a head portion thereof with a sample feed portion (12). The cylindrical tube of the inner tube (11) is designed so as to have a smaller outer diameter than an inner diameter of the outer tube (14) and a smaller length than a depth of the outer tube (14) in order to ensure a clearance for passing a gas between an outer peripheral surface of the cylindrical tube and an inner peripheral surface of the outer tube (14). In addition, the inner tube (11) is provided at a lower end thereof with a number of pores for retaining the sample (P) and withdrawing a decomposed gas to thereby render the tube air-permeable.

The sample feed portion (12) is constituted of a short cylindrical casing having a larger diameter than that of the below-mentioned outer tube (14). The casing is provided at an upper end thereof with a lid which is opened and closed to charge the sample (P) thereinto and withdraw the same therefrom. The inner tube (11) is provided at a head portion thereof, i.e., at the sample feed portion (12), with an inlet port (13) for introducing air or oxygen for burning the sample thereinto.

The outer tube (14) is constituted from an elongated bottom-closed cylindrical tube having a smaller diameter than that of the sample feed portion (12) of the above inner tube (11). The outer tube (14) is provided at an upper portion thereof with a sampling gas outlet port (15) for withdrawing hydrogen chloride generated by burning the sample. The upper end of the outer tube (14) has a threaded portion to which a lower end of the sample feed portion (12) of the inner tube (11) is screw-fitted in a hermetically sealed manner when the inner tube (11) is inserted into the outer tube.

More specifically, the reaction tube (1) is constructed such that air or oxygen is fed from the inlet port (13) into the inner tube (11), and hydrogen chloride generated upon burning a chlorine compound contained in the sample (P) is flowed together with an excess amount of air or oxygen into the outer tube (14) and further into the clearance between the outer tube (14) and the inner tube (11), and withdrawn from the sampling gas outlet port (15). Meanwhile, the inner tube (11) has a diameter of about 20 to 40 mm, and the cylindrical tube of the inner tube (11) has a length of about 350 to 400 mm. Whereas, the outer tube (14) has a diameter of about 30 to 50 mm and a length of about 400 to 450 mm.

The electric furnace (9) serves as a heating means for heating the reaction tube (1). In the present invention, a vapor of acetic acid discharged from the titration cell (3) is passed through a deodorization tube (4) to heat and decompose the acetic acid therein. Therefore, as shown in FIG. 1, the electric furnace is constructed so as to heat the deodorization tube (4) together with the reaction tube (1). More specifically, as shown in FIGS. 1 and 2, the electric furnace (9) is provided with a reaction tube insertion hole (91) opened at an upper end of the electric furnace, and heaters (93) are disposed around the reaction tube insertion hole (91). Further, the electric furnace (9) has a deodorization tube insertion hole (94) opened at an upper end thereof in the vicinity of the reaction tube insertion hole (91).

More specifically, the electric furnace (9) has such a structure in which a heat insulating material (92) is covered with a casing (90), and a plurality of the heaters (93) are embedded within the heat insulating material (92). As the heat insulating material (92), there may be used a cylindrical molded product made of ceramic fiber, or a mixed fiber composed of ceramic fiber and alumina fiber. The heat insulating material (92) is provided along a central line thereof with the reaction tube insertion hole (91) which is opened at an upper end thereof and has a circular section. Further, in the heat insulating material, the deodorization tube insertion hole (94) which is opened at an upper end thereof and has a rectangular section is formed in parallel with the above reaction tube insertion hole (91) and on an outer peripheral side of the heaters (93).

As described below, the heating temperature of the reaction tube (1) is 800 to 1100° C., whereas the heating temperature of the deodorization tube (4) is 500 to 800° C. For this reason, in the heat insulating material (92), the deodorization tube insertion hole (94) is formed at such a position located on an outer peripheral side of the heaters (93) and spaced, for example, by about 10 to 20 mm apart from the heaters (93), as shown in FIG. 2. Meanwhile, the thickness of the heat insulating material (92) (radial distance from a circumferential surface of the reaction tube insertion hole (91) to an outer peripheral surface of the heat insulating material (92)) is about 40 to 50 mm, and a bulk density thereof is about 290 to 350 kg/m$^3$ when the heat insulating material is made of a ceramic fiber.

As the heaters (93), there may be used, for example, a sheathed heater formed by accommodating a kanthal heat generator, a nichrome heat generator, a silver heat generator, etc., within a metal tube. Such heaters (93) are disposed around the reaction tube insertion hole such that the surface of each heater is exposed to the reaction tube insertion hole (91). Meanwhile, in the chlorine analyzing apparatus of the present invention, ten to twelve heaters (93) are disposed such that a total output power thereof is, for example, 1 kW. Although not shown in the drawings, the temperature of the reaction tube (1) is detected to control an electric current fed to the heaters (93) for keeping the reaction tube (1) at a predetermined temperature.

As describe above, the electric furnace (9) is provided with the reaction tube insertion hole (91) opened at an upper end of the electric furnace. The reaction tube (1) has the inner tube (11) provided at a head portion thereof with the inlet port (13) for air or oxygen, and the outer tube (14) provided at an upper portion thereof with the sampling gas inlet port (15), and is detachably fitted into the reaction tube insertion hole (91) of the electric furnace (9) from above. Therefore, in the chlorine analyzing apparatus of the present invention, the reaction tube (1) can be extremely readily replaced with new one, resulting in facilitated handling and maintenance. In addition, since an operating space required becomes small, the apparatus of the present invention can be reduced in size.

Also, as shown in FIG. 3, at a rear stage of the reaction tube (1) (on a downstream side of a flowing direction of a sampled gas), in order to dehydrate and wash hydrogen chloride withdrawn from the reaction tube (1), there is disposed a dehydration bath (2) filled, for example, with concentrated sulfuric acid as a dehydrating agent. More specifically, the sampling gas outlet port (15) of the outer tube (14) of the reaction tube (1) is connected to the dehydration bath (2) through a flow path (81).

The titration cell (3) is disposed at a rear stage of the above dehydration bath (2). More specifically, the dehydration bath (2) is connected to the titration cell (3) through a flow path (82) whose base end is located in a gas phase portion (air space portion) of the dehydration bath. The other tip end of the flow path (82) is immersed in an electrolyte filled in the titration cell (3). The titration cell (3) is filled with 70 to 90% acetic acid as the electrolyte, and serves as a device for subjecting hydrogen chloride withdrawn from the reaction tube (1) to coulometric titration. The titration cell (3) may be operated by a known mechanism, and is provided therein with a generating electrode, a generating counter electrode, a detection electrode and a reference electrode which are immersed in the electrolyte.

Upon the coulometric titration in the titration cell (3), hydrogen chloride generated from the sample (P) is adsorbed into acetic acid as the electrolyte, and titrated with silver ions coulometrically generated to measure a quantity of electricity required therefor and calculate an amount of chlorine from the measured value on the basis of Faraday Rule. More specifically, upon the above coulometric titration, an electric current for electrolysis flowed between the silver generating electrode and the generating counter electrode is controlled such that a potential of the electrolyte is maintained at a predetermined potential (terminal potential), thereby not only maintaining an equilibrium between ($Ag^+$) and ($e^-$) but also causing the reaction represented by the formula: $HCl+Ag^+ \rightarrow AgCl+H^+$ by introducing hydrogen chloride into the cell. When the potential of the electrolyte is varied, the electric current for electrolysis flowed is controlled such that the potential of the electrolyte is returned to the terminal potential, thereby generating silver ions ($Ag^+$) from the silver generating electrode. Then, at the stage at which the potential of the electrolyte is returned to the terminal potential and, therefore, the electric current for electrolysis is equal to a blank current, the titration is terminated to calculate an amount of chlorine from the quantity of electricity required for the titration. Meanwhile, the amount of acetic acid previously filled in the titration cell (3) is 20 to 40 mL.

Also, in the titration cell (3), a vapor of acetic acid as the electrolyte is generated by the above titration procedure. The titration cell (3) is equipped at a discharge port thereof with a cooler (31) for cooling the vapor of acetic acid discharged from the titration cell. As the cooler (31), there may be used, for example, a coiled condenser constituted of a coiled tube enclosed in a casing for allowing the vapor of acetic acid to pass therethrough. Although not shown in the drawings, the cooler (31) is constructed such that cold water is fed, for example, from a small-size electronic cooler using a Peltier element.

As is known in the art, the Peltier element is an electronic part used as a cooler for electronic devices, and is constituted from two metal plates and a large number of P-type semiconductors and N-type semiconductors disposed between the two metal plates in which one metal plate forms an N-P junction whereas the other metal plate forms a P-N junction. In the Peltier element, when an electric current is flowed through the P-N junction portion, an endothermic phenomenon is caused at the one metal plate. In the present invention, by disposing the above cooler (31), at least a part of acetic acid discharged in the form of a vapor from the titration cell (3) can be liquefied and circulated to the titration cell (3), so that the amount of the vapor of acetic acid to be treated in the below-mentioned deodorization tube (4) can be reduced, and reduction in amount of acetic acid as the electrolyte in the titration cell (3) can be prevented.

The deodorization tube (4) is disposed at a rear stage of the titration cell (3) for decomposing the vapor of acetic acid discharged from the titration cell (3). More specifically, the discharge port of the titration cell (3) is connected to the deodorization tube (4) through the above cooler (31) and a flow path (83). The deodorization tube (4) is fitted into the deodorization tube insertion hole (94) of the electric furnace (9) so as to thermally decompose the vapor of acetic acid.

More specifically, as shown in FIG. 1, the deodorization tube (4) is constituted of a U-shaped tube provided at an upper end thereof with a gas inlet port (pipe joint) and a gas outlet port (pipe joint). The deodorization tube insertion hole (94) is opened at an upper end of the electric furnace (9) as described above, so that the deodorization tube (4) is fitted into the deodorization tube insertion hole (94) from above. Therefore, in the chlorine analyzing apparatus of the present invention, maintenance and control of the deodorization tube (4) can be extremely readily performed. In addition, since a space required for operation of the deodorization tube (4) is small, the apparatus can be reduced in size.

The deodorization tube (4) is filled with a heat-resistant filler such as a metal oxide catalyst in order to prolong the time required for allowing the vapor of acetic acid discharged from the titration (3) to pass therethrough and thereby ensure thermal decomposition thereof. The deodorization tube (4) usually has a diameter of about 4 to 8 mm and a length of about 200 to 400 mm. The amount of the filler filled in the deodorization tube (4) may be controlled to about 0.2 to 2 g.

As shown in FIG. 3, in order to more safely discharge carbon dioxide gas and water finally generated by the thermal decomposition of the vapor of acetic acid in the deodorization tube (4), i.e., in order to surely remove malodor components even when a trace amount of acetic acid remains therein, at a rear stage of the deodorization tube (4), there are disposed a dehydration bath (5) for dehydration and gas-washing, a dryer (6) for separating water using a hollow yarn membrane and a removing device (7) constituted, for example, from alkali-supporting diatomaceous earth.

More specifically, a gas discharge port of the deodorization tube (4) is connected to the dehydration bath (5) through a flow path (84), and the dehydration bath (5) is connected at a rear stage thereof to the dryer (6) through a flow path (85). Further, the dryer (6) is connected at a rear stage thereof to the removing device (7) through a flow path (86). In order to keep a flow rate of the gas circulated through the system constant, in other words, in order to introduce hydrogen chloride as a sample into the titration cell (3) at a constant flow rate and discharge the vapor of acetic acid from the titration cell (3) at a constant flow rate, the removing device (7) located at a most downstream side of the system may be further connected to a vacuum pump (8) such as a rotary pump through a flow path (87) equipped with a flow control needle valve.

Next, functions of the chlorine analyzing apparatus of the present invention are explained. Upon the measurement of a trace amount of chlorine using the chlorine analyzing apparatus of the present invention, as shown in FIG. 3, activated carbon in which a chlorine compound is adsorbed, i.e., the sample (P), is first charged into the inner tube (11) of the reaction tube (1). The amount of the sample (P) to be charged is usually about 0.02 to 0.1 g. Then, air or oxygen is fed into the inner tube (11) of the reaction tube (1) through the inlet port (13) for air or oxygen. The air or oxygen is fed in a constant amount under a constant pressure through a flow path (not shown) equipped with a pressure reducing valve and a flow control valve from a container in which air or oxygen is filled in a compressed state. Specifically, the air or oxygen is fed under a pressure of 1 to 3 MPa at a flow rate of 1 to 2 L/min.

Next, the electric furnace is energized such that an inside of the reaction tube (1) is heated to a temperature of 800 to 1100° C. by the heaters (93). When heating the reaction tube (1), the chlorine compound contained in the sample (P) filled in the inner tube (11) is burned under an air or oxygen gas flow to produce hydrogen chloride. The thus generated hydrogen chloride is flowed together with an excess amount of air or oxygen into the outer tube (14) and then into the clearance between the outer tube (14) and the inner tube (11), and finally withdrawn through the sampling gas outlet port (15) of the outer tube (14).

The hydrogen chloride thus obtained in the reaction tube (1) is delivered to the dehydration bath (2) where the gas is subjected to dehydration treatment, and then introduced into the titration cell (3). In the titration cell (3), the hydrogen chloride is blown into acetic acid as the electrolyte and subjected to coulometric titration by the above-described method. Upon the coulometric titration, a quantity of an electric current flowed through the electrode during the titration is measured, and an amount of chlorine is calculated from the measured value using a computer separately provided. Thus, the result of the titration is expressed by the value as measured in terms of chlorine.

On the other hand, when air or oxygen is fed to the reaction tube (1), the vacuum pump (8) is simultaneously operated. While feeding air or oxygen to the reaction tube (1) and conducting the titration procedure in the titration cell (3), a part of the vapor of acetic acid discharged from the titration cell (3) is captured by the cooler (31) and circulated to the titration cell (3). The other part of the vapor of acetic acid is introduced into the deodorization tube (4) through the flow path (83) and subjected to decomposition treatment in the deodorization tube (4). In the present invention, since the deodorization tube (4) is accommodated in the electric furnace (9) as described above, the deodorization tube (4) is heated to a temperature of not less than 440° C. and preferably 600 to 800° C., so that the vapor of acetic acid fed thereto is thermally decomposed, and carbon dioxide gas and water are discharged from the deodorization tube (4). In order to more surely treat a trace amount of acetic acid, the carbon dioxide gas and water discharged from the deodorization tube (4) are then delivered to the dehydration bath (5) and the dryer (6) to remove water therefrom, and then delivered to the removing device (7) to render the discharged gas harmless.

As described above, in the chlorine analyzing apparatus of the present invention, since the deodorization tube (4) is accommodated within the electric furnace (9) for heating the reaction tube, the deodorization tube (4) can be heated by utilizing heat generated from the electric furnace (9), so that the vapor of acetic acid discharged from the titration cell (3) can be thermally decomposed. Thus, since the vapor of acetic acid is surely treated, it is possible to prevent malodor from being released from the apparatus. In addition, since provision of a separate heating means is not required, the treatment can be surely and efficiently conducted without increase in size of the apparatus.

According to the chlorine analyzing apparatus of the present invention, since the deodorization tube is accommodated within the electric furnace for heating the reaction tube, the deodorization tube can be heated by utilizing heat generated from the electric furnace to thermally decompose the vapor of acetic acid discharged from the titration cell. As a result, the vapor of acetic acid can be surely treated without increase in size of the apparatus.

What is claimed is:

1. A chlorine analyzing apparatus for measuring an amount of chlorine contained in a sample by subjecting hydrogen chloride generated by heating the sample to coulometric titration, which apparatus comprises:
   a reaction tube of a double tube structure comprising an inner tube with an inlet port for air or oxygen for receiving the sample, and an outer tube with a sampling gas outlet port for recovering hydrogen chloride, the reaction tube being capable of allowing a gas to be flowed from the inner tube to the outer tube;
   an electric furnace having a reaction tube insertion hole into which the reaction tube is fitted, the electric furnace being equipped with a heater disposed around the reaction tube insertion hole;
   a titration cell receiving acetic acid as an electrolyte for subjecting hydrogen chloride withdrawn from the reaction tube to coulometric titration; and
   a deodorization tube disposed on a rear stage side of the titration cell for thermally decomposing a vapor of acetic acid discharged from the titration cell, the deodorization tube being fitted into a deodorization tube insertion hole in the electric furnace,
   wherein the deodorization tube insertion hole in the electric furnace is positioned on an outer peripheral side of the heater and is spaced therefrom so as to control a heating temperature of the deodorization tube to 500 to 800° C. when a heating temperature of the reaction tube is 800 to 1100° C.

2. A chlorine analyzing apparatus according to claim 1, wherein the deodorization tube is constituted from a U-shaped tube with a gas inlet port and a gas outlet port, and is detachably fitted into the deodorization tube insertion hole of the electric furnace from above.

3. A chlorine analyzing apparatus according to claim 2, wherein the electric furnace is provided with the reaction tube insertion hole opened at an upper end of the electric furnace, and the reaction tube is provided at a head portion of the inner tube with the inlet port for air or oxygen and at an upper portion of the outer tube with the sampling gas outlet port, and detachably fitted into the reaction tube insertion hole of the electric furnace from above.

4. A chlorine analyzing apparatus according to claim 1, wherein the deodorization tube is filled with a heat-resistant filler.

5. A chlorine analyzing apparatus according to claim 2, wherein the deodorization tube is filled with a heat-resistant filler.

6. A chlorine analyzing apparatus according to claim 3, wherein the deodorization tube is filled with a heat-resistant filler.

7. A chlorine analyzing apparatus according to claim 1, wherein the titration cell has a discharge port to which a cooler for cooling a vapor of acetic acid discharged from the titration cell is fitted.

8. A chlorine analyzing apparatus according to claim 2, wherein the titration cell has a discharge port to which a cooler for cooling a vapor of acetic acid discharged from the titration cell is fitted.

9. A chlorine analyzing apparatus according to claim 3, wherein the titration cell has a discharge port to which a cooler for cooling a vapor of acetic acid discharged from the titration cell is fitted.

10. A chlorine analyzing apparatus according to claim 4, wherein the titration cell has a discharge port to which a cooler for cooling a vapor of acetic acid discharged from the titration cell is fitted.

11. A chlorine analyzing apparatus according to claim 5, wherein the titration cell has a discharge port to which a cooler for cooling a vapor of acetic acid discharged from the titration cell is fitted.

12. A chlorine analyzing apparatus according to claim 6, wherein the titration cell has a discharge port to which a cooler for cooling a vapor of acetic acid discharged from the titration cell is fitted.

13. A chlorine analyzing apparatus according to claim 1, wherein a heat insulating material is placed between the outer peripheral side of the heaters and the reaction tube insertion hole.

14. A chlorine analyzing apparatus according to claim 1, wherein the heater is a sheathed heater formed by accommodating a kanthal heat generator, a nichrome heat generator or a silver heat generator within a metal tube.

* * * * *